US012778919B2

(12) United States Patent
Duan et al.

(10) Patent No.: US 12,778,919 B2
(45) Date of Patent: Nov. 3, 2026

(54) SMALL MOLECULE MELPHALAN HYDROGEL AND METHOD FOR PREPARING THE SAME

(71) Applicant: Changzhi Medical College, Changzhi City (CN)

(72) Inventors: Xiao Duan, Changzhi City (CN); Ting Li, Changzhi City (CN); Kai Yuan, Changzhi City (CN); Ningyue Lu, Changzhi City (CN); Yanbin He, Changzhi City (CN); Junbo Li, Changzhi City (CN)

( * ) Notice: Subject to any disclaimer, the term of this patent is extended or adjusted under 35 U.S.C. 154(b) by 335 days.

(21) Appl. No.: 18/769,364

(22) Filed: Jul. 10, 2024

(65) Prior Publication Data

US 2024/0358665 A1 Oct. 31, 2024

(51) Int. Cl.
*A61K 31/198* (2006.01)
*A61K 9/06* (2006.01)

(52) U.S. Cl.
CPC .............. *A61K 31/198* (2013.01); *A61K 9/06* (2013.01)

(58) Field of Classification Search
CPC ................................ A61K 31/198; A61K 9/06
See application file for complete search history.

(56) References Cited

PUBLICATIONS

Alexander, Amit, et al. "Formulation and evaluation of chitosan-based long-acting injectable hydrogel for PEGylated melphalan conjugate." Journal of Pharmacy and Pharmacology 66.9 (2014): 1240-1250. (Year: 2014).*

* cited by examiner

*Primary Examiner* — James H Alstrum-Acevedo
*Assistant Examiner* — Justin Christopher Sanchez

(57) ABSTRACT

The present disclosure relates to the field of hydrogel technology, and specifically relates to a small molecule melphalan hydrogel and a preparation method thereof. The small molecule melphalan hydrogel is made of melphalan drug or melphalan hydrochloride as raw materials, and it is formed at room temperature or physiological condition by means of making the melphalan drug in a hydrophilic solvent. The hydrophilic solvent includes any one of physiological saline, pure water, and phosphate buffered saline solution. The small molecule melphalan hydrogel provided by the present disclosure is an injectable hydrogel of 100% pure melphalan drug, the gel only contains small molecule melphalan drug, which solves the problems of containing a large amount of carrier materials and having a low drug loading rate in the field of hydrogel.

8 Claims, 8 Drawing Sheets

Melphalan

Mephalan sodium salt

A B solution state gel state

SMALL MOLECULE MELPHALAN HYDROGEL AND METHOD FOR PREPARING THE SAME

CROSS-REFERENCE TO RELATED APPLICATION

This application claims priority to Chinese Patent Application No. 202410135249.7, filed on Jan. 31, 2024 before the China National Intellectual Property Administration, the disclosure of which is incorporated herein by reference in entirety.

TECHNICAL FIELD

The present disclosure relates to the field of hydrogel, and in particular to a small molecule melphalan hydrogel and a method for preparing the same.

BACKGROUND

Hydrogel is a drug delivery system or dosage form. However, hydrogels usually contain a large amount of carrier materials. Small molecule hydrogels can avoid the use of a large amount of carrier materials and effectively avoid the toxic and side effects of carrier materials on normal tissues. Melphalan, also known as alkeran, is an anti-tumor drug that is effective for multiple myeloma, breast cancer, ovarian cancer, chronic lymphocytic and granulocytic leukemia, and malignant lymphoma. The main clinical administration methods include oral, intravenous or drip administration. The commonly used clinical administration methods of melphalan are highly toxic to normal tissues, and the drug is metabolized rapidly in the body, and therefore it cannot inhibit tumors in a long period. Therefore, it is necessary to develop a new dosage form of melphalan to solve the problems of the common administration methods of melphalan mentioned above.

So far, there has been no development of pure drug hydrogel preparations for small molecule melphalan drugs. Although there is no hydrogel specifically for small molecule melphalan drugs, there are drug hydrogels that are common to conventional drugs. Drug hydrogels can avoid the use of carrier materials and increase the duration of drug action in the lesion site, while avoiding toxic side effects on normal tissues. However, the drug-containing hydrogels designed at this stage use a large amount of carrier materials in the preparation process, such as chitosan, poloxamer, and polyethylene glycol, the prepared hydrogels contain a large amount of carrier materials and have a low drug loading rate. Since the drug-containing hydrogels designed at this stage contain a large amount of carrier materials, they will have toxic side effects on normal tissues and they are not suitable for in situ injection. Therefore, in view of the problem that the drug-containing hydrogels designed at this stage contain a large amount of carrier materials and have a low drug loading rate, and they are not suitable for small molecule melphalan drugs, we need to develop a 100% drug hydrogel that can be injected in situ and is suitable for small molecule pure melphalan drugs.

SUMMARY

In order to solve the problem that the drug hydrogels currently designed in the prior art contain a large amount of carrier materials and have a low drug loading rate, and they are not suitable for small molecule melphalan drugs, the present disclosure provides a 100% drug melphalan hydrogel that can be injected in situ and a preparation method thereof to avoid the toxic side effects of small molecule melphalan drugs and prolong the duration of action on tumors. To achieve the above purpose, the present disclosure adopts the following technical solutions.

The present disclosure provides a small molecule melphalan hydrogel, wherein the small molecule melphalan hydrogel is made of melphalan drug or melphalan hydrochloride as raw materials, and the small molecule melphalan hydrogel is formed at room temperature or physiological condition by means of making the melphalan drug in a hydrophilic solvent;

- wherein the hydrophilic solvent comprises any one of physiological saline, pure water, and phosphate buffered saline solution.

The small molecule melphalan hydrogel is a 100% drug hydrogel of pure melphalan that can be injected in situ; the hydrophilic solvent is used to form a hydrophilic environment to make melphalan form a gel state, but it is not used as a carrier for preparing the hydrogel.

The present disclosure further provides a method for preparing the small molecule melphalan hydrogel, comprising the following steps:

- taking the melphalan drug, adding the hydrophilic solvent to dissolve the melphalan drug, obtain a melphalan solution;
- placing the melphalan solution at room temperature or physiological condition for 5 minutes to 1.5 hours, to allow the melphalan solution to form a gel state, and thereby obtaining the small molecule melphalan hydrogel.

According to some embodiments of the present disclosure, if the hydrophilic solvent is pure water, a NaOH aqueous solution is used to dissolve melphalan to obtain the melphalan solution.

According to some embodiments of the present disclosure, a mass percentage of the melphalan drug to the NaOH aqueous solution is 1% to 30%.

According to some embodiments of the present disclosure, if the hydrophilic solvent is physiological saline, then the physiological saline is used to dissolve melphalan, and a high-concentration NaOH aqueous solution is used to adjust melphalan to a sodium salt form to obtain the melphalan solution.

According to some embodiments of the present disclosure, a concentration of the high-concentration NaOH aqueous solution is 0.1 to 5 mmoL/mL.

According to some embodiments of the present disclosure, a mass percentage of the melphalan drug to the physiological saline is 1% to 30%.

According to some embodiments of the present disclosure, if the hydrophilic solvent is phosphate buffered saline solution, the phosphate buffered saline solution is used to dissolve melphalan for obtaining the melphalan solution, and a content of melphalan in the solution is 2.5%.

According to some embodiments of the present disclosure, a mass percentage of the melphalan drug to the phosphate buffered saline solution is 2.5% to 30%.

Compared with the prior art, the present disclosure has the following beneficial effects:

I. The present disclosure provides a small molecule melphalan hydrogel, which is an injectable hydrogel of 100% pure melphalan drug, wherein the gel contains only small molecule melphalan drug, which overcomes the shortcomings of containing a large amount of carrier materials and having a low drug loading rate in the field of hydrogel.

II. In order to avoid the toxic side effects of the anti-tumor drug melphalan and prolong the action time on tumors, the present disclosure prepares a 100% drug melphalan hydrogel that can be injected in situ. By adjusting the proportion of carboxylates in the melphalan structure, the gel time of the pure-drug small molecule melphalan hydrogel is controlled, laying a preliminary foundation for the development of new drug hydrogel preparations.

III. The present disclosure further provides a method for preparing the small molecule melphalan hydrogel, and the preparation method can be used to construct a new small molecule melphalan pure-drug hydrogel preparation (dosage form). The preparation method provided by the present disclosure can achieve the preparation of drug hydrogel by simply adjusting the ratio of carboxylates in the melphalan drug structure, and therefore the preparation method is very simple. At the same time, the small molecule melphalan hydrogel provided by the present disclosure does not contain any other ingredients except the drug, which is beneficial to clinical application. In addition, the prepared small molecule melphalan hydrogel completes the form of hydrogel within 5 minutes in physiological saline, pure water, and phosphate buffered saline solution (phosphate buffer solution) at room temperature or physiological condition, which is beneficial to the development and utilization of injectable hydrogels.

DETAILED DESCRIPTION OF EMBODIMENTS

The present disclosure will be described in detail below in conjunction with the accompanying drawings and specific embodiments, but it should not be construed as limiting the present disclosure. Unless otherwise specified, the technical means used in the following embodiments are conventional means known to those skilled in the art, and the materials, reagents, etc. used in the following embodiments, unless otherwise specified, can all be obtained from commercial channels.

The following are the reagents and instruments used in the embodiments:

(1) Drugs

Figure 1:
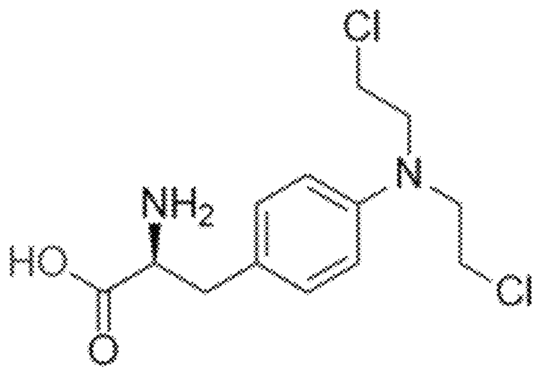
FIG. 1 shows the structure of mephalan in the present disclosure.
Figure 2:
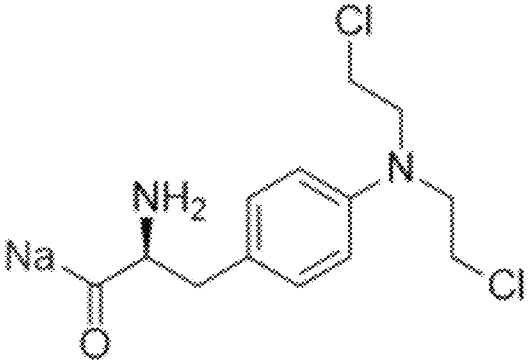
FIG. 2 shows the structure of mephalan sodium salt in the present disclosure.

Melphalan drugs were purchased from Wuhan Yuancheng Co., Ltd. The structures of melphalan and melphalan sodium salt are shown in FIGS. 1 and 2, respectively.

(2) Reagents

NaOH was purchased from Changzhi Jinbaiao Biotechnology Co., Ltd.; 0.9% NaCl solution (physiological saline) was purchased from Changzhi Jinbaiao Biotechnology Co., Ltd.; PBS (phosphate buffered saline, or called as phosphate buffer solution) was purchased from Biyuntian Biotechnology Co., Ltd., the concentration of PBS was 10 mM, with pH of 7.4.

(3) Instruments

Air blast drying oven: Changzhi Jinbaiao Biotechnology Co., Ltd.; UV spectrophotometer: Beijing Puxi, TU1901.

Embodiment 1

Figure 3:
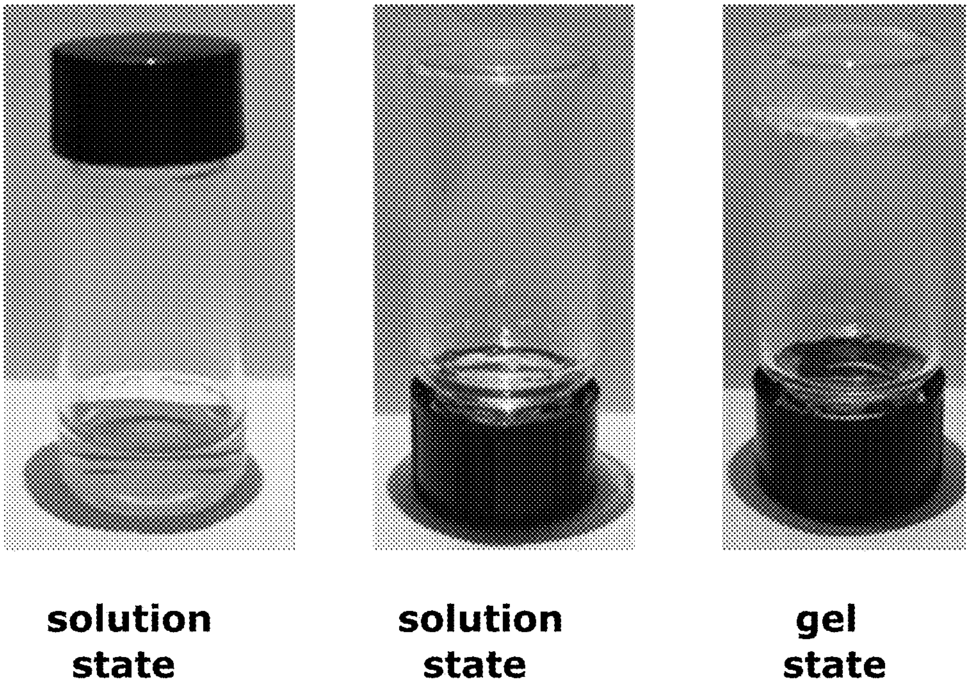
FIG. 3 shows the drug hydrogel in pure water when the content of mephalan is 1.5% in the present disclosure.

A method for preparing a small molecule melphalan hydrogel, comprising the following steps:

Weigh 0.1 mmoL of melphalan drug, use 1.5 mL of NaOH aqueous solution with a concentration of 0.15 mmoL/mL to dissolve melphalan to obtain a melphalan solution; after the melphalan solution is placed at room temperature for 1 hour, the solution becomes a gel state, and a small molecule melphalan hydrogel is obtained. At the same time, in the process of transformation from solution state to gel state, the time and morphology of small molecule melphalan drug into hydrogel are observed and recorded, and the time of hydrogel formation is determined by observing the fluidity of solution state. The prepared small molecule melphalan hydrogel is shown in FIG. 3.

Herein, the mass percentage of melphalan drug to NaOH aqueous solution is 2%.

In order to further verify whether the above melphalan solution can form hydrogel in tissue, a 2% melphalan solution is injected into the subcutaneous part of pork and it is placed in a 37° C. oven for 10 minutes to observe whether the 2% melphalan solution is still in solution state. After it seems a hydrogel block is formed, the hydrogel block under the pork skin is taken out, to prove that the melphalan solution can form hydrogel in tissue, the results are shown in FIG. 6.

Figure 6:
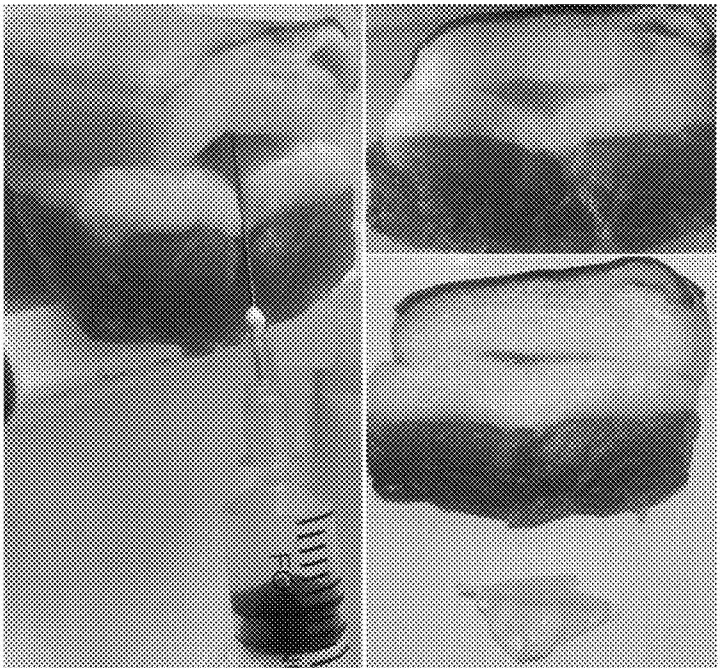
FIG. 6 shows the gelation process of mephalan (2%) solution injected into pork skin in the present disclosure; wherein A refers to melphalan in solution state injected into the subcutaneous part of pork; B refers to that the melphalan in solution state in the pork becomes gel state after waiting for 10 minutes in a 37 degree environment.

As shown in FIG. 6, the melphalan is dissolved in the corresponding NaOH aqueous solution in a flowing liquid state. When it is injected into the subcutaneous tissue, it can be transformed into a non-fluid gel state within 10 minutes. This experimental result proves that melphalan in gel state can be retained in the subcutaneous tissue for a longer time.

Embodiment 2

Figure 4:
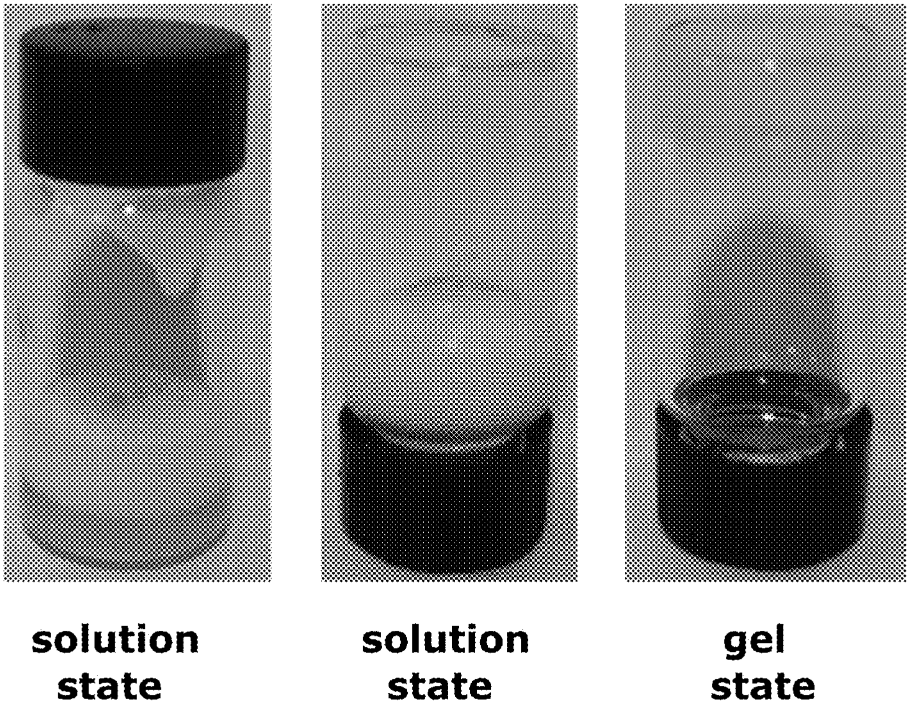
FIG. 4 shows the drug hydrogel in 0.9% NaCl solution (normal saline) when the content of melphalan is 2% in the present disclosure.

A method for preparing a small molecule melphalan hydrogel, comprising the following steps:

Weigh 0.1 mmoL of melphalan drug, use 1.45 mL of 0.9% NaCl solution (normal saline, physiological saline) to dissolve melphalan, and use 50 μL of 2 mmoL/mL high concentration NaOH aqueous solution to adjust melphalan to sodium salt form to form a melphalan solution; after the melphalan solution is placed at room temperature for 1 hour, the solution changes to a gel state, obtaining a small molecule melphalan hydrogel. At the same time, in the process of transformation from solution state to gel state, the time and morphology of the small molecule melphalan drug into a hydrogel are observed and recorded, and the time of forming a hydrogel is determined by observing the fluidity of the solution state. The prepared small molecule melphalan hydrogel is shown in FIG. 4.

Herein, the structures of melphalan and melphalan sodium salt are shown in FIG. 1.

The dosage ratio of melphalan drug to 0.9% NaCl solution is 1.5%.

Embodiment 3

Figure 7:
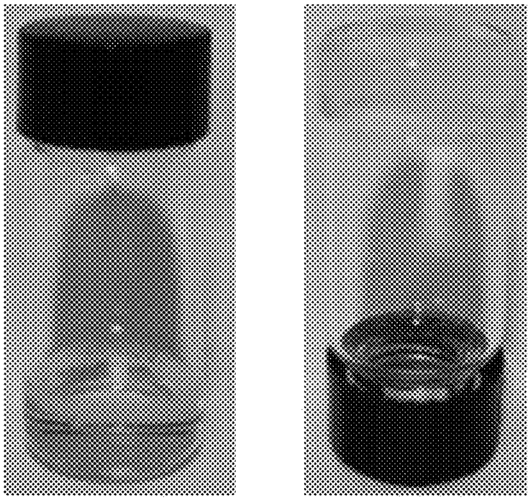
FIG. 7 shows the drug hydrogel in phosphate buffered saline (PBS) when the content of melphalan is 2.5% in the present disclosure.

A method for preparing a small molecule melphalan hydrogel, comprising the following steps:

Weigh the melphalan drug, dissolve it in PBS (phosphate buffered saline) so that the content of melphalan in the solution is 2.5%, and dissolve it with ultrasound assistance to form a melphalan solution; after the melphalan solution is placed at room temperature for 1 hour, the solution changes to a gel state, and a small molecule melphalan hydrogel is obtained. At the same time, in the process of transformation from the solution state to the gel state, the time and morphology of the small molecule melphalan drug into a hydrogel are observed and recorded, and the time of forming a hydrogel is determined by observing the fluidity of the solution state. The prepared small molecule melphalan hydrogel is shown in FIG. 7.

Herein, the concentration of PBS is 10 mM and the pH of PBS is 7.4.

The dosage ratio of melphalan drug to PBS is 2.5%.

In order to further verify whether the above melphalan solution can form hydrogel in tissue, a 2.5% melphalan solution is injected into the subcutaneous part of a rat and it is placed in a 37° C. oven for 10 minutes. After 10 minutes, the skin of the rat is cut open to observe whether the 2.5% melphalan solution is still in solution state. After it seems a hydrogel block is formed, the hydrogel block under the skin of the rat is taken out, to prove that the melphalan solution can form hydrogel in tissue. The experimental process and results are shown in FIG. 8.

Figure 8:
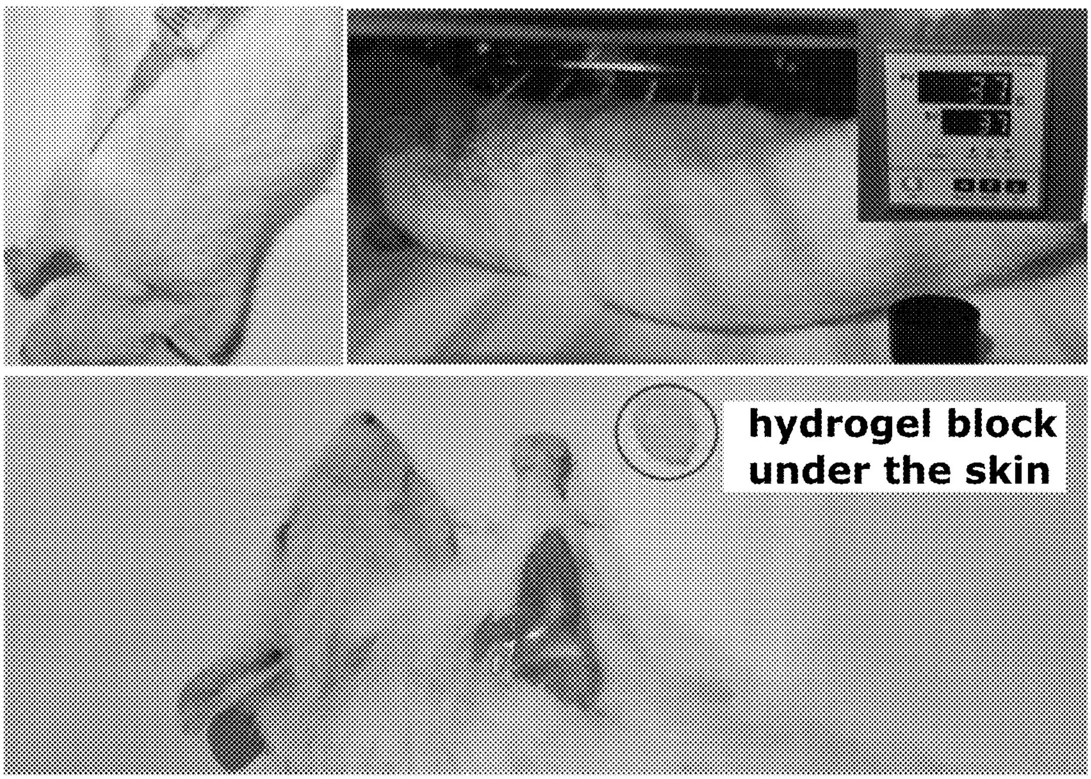
FIG. 8 shows the drug gel state after 2.5% melphalan is dissolved in phosphate buffered saline (PBS) and injected under the skin of a rat for 10 minutes in the present disclosure; wherein A refers to the process of injecting melphalan solution into the subcutaneous part of the rat; B refers to the process of treating the rat in a 37 degree oven for 10 minutes; C refers to a picture showing that the melphalan solution under the skin of the rat after 10 minutes becomes a melphalan gel block.

As shown in FIG. 8, melphalan is dissolved in the corresponding phosphate buffered saline solution in a flowing liquid state. When it is injected into the subcutaneous tissue, it can be transformed into a non-fluid gel state within 10 minutes. This experimental result proves that melphalan in gel state can be retained in the subcutaneous tissue for a longer time.

The small molecule melphalan hydrogels prepared in Embodiments 1 to 3 of the present disclosure are tested for transmittance, and the specific testing steps are as follows:

Prepare small molecule melphalan solutions according to the methods in Embodiments 1 to 3 above, take 3 mL of the solution and place it in a glass dish, and place the glass dish in an ultraviolet spectrophotometer, and measure the change of transmittance over time, at 790 nm. The phenomenon that the transmittance gradually decreases from 100% (solution state) to less than 10% proves that the small molecule melphalan solution is transformed into a hydrogel. The measured results are shown in FIG. 5.

Figure 5:
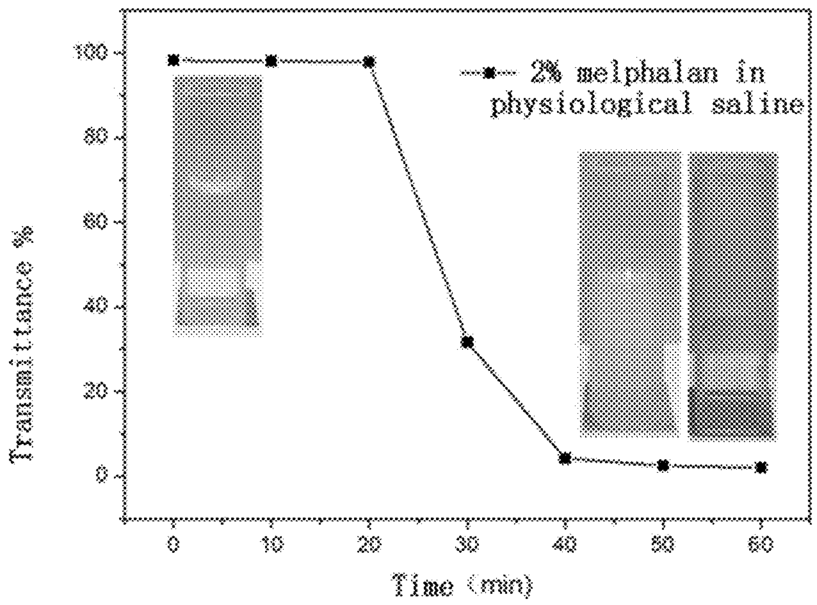
FIG. 5 shows the change of transmittance over time, measured by UV-visible spectrophotometer at 790 nm when the melphalan is in 0.9% NaCl with content of 2% in the present disclosure.

As shown in FIG. 5, after melphalan is dissolved in physiological saline to form a transparent liquid, it is placed in an ultraviolet spectrophotometer and its transmittance is detected at 790 nm. As time goes by, it can be found that the transmittance changes from 100% to less than 10%, indicating that the melphalan in the solution state has become a hydrogel.

It can be seen from the above results that the small molecule melphalan hydrogel provided by the present disclosure is a pure-melphalan hydrogel with potential clinical application value. The preparation method of the small molecule melphalan hydrogel provided by the present disclosure is simple and practical.

The steps of the preparation method of the small molecule melphalan hydrogel provided in Embodiments 1 to 3 of the present disclosure include: forming a hydrogel at room temperature or 37° C. after preparing the small molecule melphalan solution. The time for forming the hydrogel can be controlled by adjusting the proportion of carboxylates in melphalan.

The present disclosure analyses a preparation method of hydrogel disclosed in "A comparative study of chitosan and poloxamer based thermosensitive hydrogel for the delivery of PEGylated melphalan conjugates" (DOI: 10.3109/03639045.2015.1011167; DOI: 10.1111/jphp. 12262). The preparation method is to first prepare PEGylated melphalan, then prepare a hydrogel of chitosan or poloxamer, and then blend it with the PEGylated melphalan in the process of forming the gel. When preparing the drug hydrogel, the preparation process steps of this preparation method are relatively complicated, a large number of carriers are used, and the prepared drug hydrogel contains a large amount of carrier materials and has a low drug loading rate.

Compared with the above preparation method, the preparation methods of the small molecule melphalan hydrogel provided in Embodiments 1 to 3 of the present disclosure have the step of directly dissolving melphalan in an aqueous environment, and a pure drug hydrogel can be formed within 1 hour. When preparing the drug hydrogel, the preparation method of the small molecule melphalan hydrogel provided in Embodiments 1 to 3 of the present disclosure prepares a pure-drug hydrogel, which does not contain any carrier and has a high drug loading rate.

The present disclosure also refers to the preparation method of hydrogel disclosed in "A small molecule gel of a Chinese herbal medicine component (rhein) with anti-inflammatory function" (nature.com/articles/s41467-019-09601-3). The preparation method is to dissolve rhein in sodium bicarbonate or PBS by ultrasonic or heating to form a homogeneous solution, and then place it at room temperature for 5 minutes, and then form a hydrogel.

Compared with the above preparation method, the preparation methods of the small molecule melphalan hydrogel provided in Embodiments 1 to 3 of the present disclosure have the steps of directly dissolving melphalan in an aqueous environment, forming a homogeneous solution, and then forming a pure drug hydrogel at 37° C. or room temperature after 5 minutes. The formed pure-drug small molecule melphalan hydrogel has an anti-tumor effect. At the same time, the melphalan drug used in the present disclosure is a small molecule anti-tumor drug approved for clinical use. Compared with the above preparation method, the monomer component of rhein has not been widely used in clinical practice. When preparing the drug hydrogel, the preparation method of the small molecule melphalan hydrogel provided in Embodiments 1 to 3 of the present disclosure prepares a pure-drug hydrogel, which does not contain any carrier and has a high drug loading rate.

The present disclosure also refers to the preparation methods of hydrogels disclosed in "Supramolecular hydrogels based on self-assembled small-molecule biofunctional nanofibers" (doi: 10.1039/B702493B), "A simple visual assay based on small molecule hydrogels for detecting inhibitors of enzymes" (DOI: 10.1039/b408897b), "Small molecule hydrogels based on first-class anti-inflammatory drugs", "Two methods for homogeneous small molecule hydrogel engineering" (DOI: 10.1039/c3sm50324k), and "A multifunctional small molecule motif for self-assembly in water and the formation of biofunctional supramolecular hydrogels" (DOI: 10.1021/la1020324 529). These preparation methods are all to first hydrophilize the carboxyl groups in the small molecules. The hydrogels prepared by these preparation methods use small molecules that are not clinically used drugs, and cannot achieve the preparation of 100% drug hydrogels.

Compared with the above preparation methods, the preparation methods of the small molecule melphalan hydrogel provided in Embodiments 1 to 3 of the present disclosure have the step of directly dissolving melphalan in an aqueous environment, forming a homogeneous solution, and then forming a pure drug hydrogel at 37° C. or room temperature after 5 minutes. There is no need to modify the small molecule drug.

Compared with the drug hydrogels prepared by the above disclosed hydrogel preparation methods, the small molecule melphalan hydrogel is a new preparation (dosage form) that can avoid the use of carrier materials and speed up clinical approval. At the same time, the preparation method of the small molecule melphalan hydrogel provided by the present disclosure has the advantages of being simple and convenient and easy to use clinically, and it can expand the scope of clinical application of melphalan drugs.

The present disclosure provides a small molecule melphalan hydrogel, which is an injectable hydrogel of 100% pure melphalan drug, wherein the gel only contains small molecule melphalan drug, which overcomes the shortcomings of containing a large amount of carrier materials and having a low drug loading rate in the field of hydrogels. At the same time, as an anti-tumor drug, the development of new preparations or new dosage forms of melphalan helps to expand the scope of clinical application of melphalan drugs. The new melphalan preparation prepared by the present disclosure, which can form a small molecule melphalan hydrogel within 5 minutes, can be injected at the tumor site or the postoperative site of the tumor, and after forming the drug hydrogel, it can exert a long-term anti-tumor effect while avoiding toxic effects on normal tissues.

It should be noted that when the numerical range is involved in the claims of the present disclosure, it should be understood that the two endpoints of each numerical range and any numerical value between the two endpoints can be selected. In order to avoid redundancy, the present disclosure describes the optional embodiments.

Although the preferred embodiments of the present disclosure have been described, additional changes and modifications can be made to these embodiments once those skilled in the art know the basic creative concept. Therefore, the attached claims are intended to be interpreted as including the preferred embodiments and all changes and modifications that fall within the scope of the present disclosure.

Obviously, various modifications and variations may be made to the present disclosure by those skilled in the art without departing from the spirit and scope of the present disclosure. Thus, if these modifications and variations of the present disclosure fall within the scope of the claims of the present disclosure and their equivalent technologies, the present disclosure is also intended to include these modifications and variations.

What is claimed is:

1. A method for preparing a small molecule melphalan hydrogel, wherein the method comprises the following steps: taking the melphalan drug, adding the hydrophilic solvent to dissolve the melphalan drug to acquire the melphalan salt form, thus obtaining a melphalan sodium salt solution; placing the melphalan solution at room temperature or physiological condition for 5 minutes to 1.5 hours, to allow the melphalan solution to form a gel state, and thereby obtaining the small molecule melphalan hydrogel.

2. The method according to claim 1, wherein if the hydrophilic solvent is pure water, a NaOH aqueous solution is used to dissolve melphalan to obtain the melphalan solution.

3. The method according to claim 2, wherein a mass percentage of the melphalan drug to the NaOH aqueous solution is 1% to 30%.

4. The method according to claim 1, wherein if the hydrophilic solvent is physiological saline, then the physiological saline is used to dissolve melphalan, and a high-concentration NaOH aqueous solution is used to adjust melphalan to a sodium salt form to obtain the melphalan solution.

5. The method according to claim 4, wherein a concentration of the high-concentration NaOH aqueous solution is 0.1 to 5 mmoL/mL.

6. The method according to claim 4, wherein a mass percentage of the melphalan drug to the physiological saline is 1% to 30%.

7. The method according to claim 1, wherein if the hydrophilic solvent is phosphate buffered saline solution, the phosphate buffered saline solution is used to dissolve melphalan for obtaining the melphalan solution, and a content of melphalan in the solution is 2.5%.

8. The method according to claim 7, wherein a mass percentage of the melphalan drug to the phosphate buffered saline solution is 2.5% to 30%.

* * * * *